(12) United States Patent
Bambang Oetomo et al.

(10) Patent No.: US 12,310,750 B2
(45) Date of Patent: May 27, 2025

(54) WEARABLE DEVICE, METHOD AND SYSTEM FOR MONITORING ONE OR MORE VITAL SIGNS OF A HUMAN BODY

(71) Applicant: Bambi Belt Holding B.V., Eindhoven (NL)

(72) Inventors: Sidarto Bambang Oetomo, Waalre (NL); Martijn ten Bhömer, Suzhou (CN); Claudia Caparelli, Eindhoven (NL)

(73) Assignee: Bambi Belt Holding B.V., Eindhoven (NL)

( * ) Notice: Subject to any disclaimer, the term of this patent is extended or adjusted under 35 U.S.C. 154(b) by 119 days.

(21) Appl. No.: 16/334,972

(22) PCT Filed: Sep. 20, 2017

(86) PCT No.: PCT/NL2017/050624
§ 371 (c)(1),
(2) Date: Mar. 20, 2019

(87) PCT Pub. No.: WO2018/056811
PCT Pub. Date: Mar. 29, 2018

(65) Prior Publication Data
US 2020/0015746 A1   Jan. 16, 2020

(30) Foreign Application Priority Data

Sep. 21, 2016 (NL) ...................................... 2017506

(51) Int. Cl.
*A61B 5/00* (2006.01)
*A61B 5/0205* (2006.01)
(Continued)

(52) U.S. Cl.
CPC .......... *A61B 5/6804* (2013.01); *A61B 5/0006* (2013.01); *A61B 5/0205* (2013.01);
(Continued)

(58) Field of Classification Search
CPC .... A61B 5/6831; A61B 5/6801; A61N 1/0484
See application file for complete search history.

(56) References Cited

U.S. PATENT DOCUMENTS

2007/0293781 A1* 12/2007 Sims ........................ A61B 5/72
600/534
2011/0060215 A1* 3/2011 Tupin, Jr. ............. A61B 5/0803
600/407

(Continued)

FOREIGN PATENT DOCUMENTS

NL           7501485 A       8/1975
WO    WO 2015/089668 A1     6/2015
(Continued)

OTHER PUBLICATIONS

Luca Mesin, et all; Separation of propagating and non propagating components in surface EMG, Biomedical Signal Processing and Control, vol. 3, Issue 2, 2008, pp. 126-137; ISSN 1746-8094 (Year: 2008).*

(Continued)

*Primary Examiner* — Gary Jackson
*Assistant Examiner* — Skylar Lindsey Christianson
(74) *Attorney, Agent, or Firm* — Leydig, Voit & Mayer, Ltd.

(57) ABSTRACT

The present document describes a wearable device for monitoring one or more vital signs of a human body, the device comprising a carrier suitable for being worn around an abdominal part of the body, and an electrode arrangement comprising a plurality of conductive electrodes, wherein the electrodes are arranged on the carrier such as to be brought in contact with a skin of the body in use, and wherein the electrodes are arranged for receiving electric physiologic signals from the body for enabling monitoring of a membrane potential of one or more muscles in the body, wherein the electrodes comprise one or more first electrodes arranged (Continued)

on the carrier such as to be in contact with a side part of a torso of the body, such as to receive via said first electrodes a first electrical signal indicative of a membrane potential of a thoracic diaphragm of the body; wherein the carrier further comprises at least one second electrode in addition to the one or more first electrodes, the at least one second electrode being arranged on the carrier such as to be in contact with a mid front part of the abdominal part of the body, the at least one second electrode thereby being arranged for receiving a second electrical signal indicative of one or more further electric physiologic signals from the body, for enabling filtering of the first electrical signal using the second electrical signal for enabling electromyography of the thoracic diaphragm.

12 Claims, 7 Drawing Sheets

(51) Int. Cl.
 *A61B 5/25* (2021.01)
 *A61B 5/389* (2021.01)
 *A61B 5/024* (2006.01)
(52) U.S. Cl.
 CPC ............... *A61B 5/25* (2021.01); *A61B 5/389* (2021.01); *A61B 5/024* (2013.01); *A61B 5/6823* (2013.01); *A61B 5/6831* (2013.01); *A61B 2503/045* (2013.01); *A61B 2562/0215* (2017.08)

(56) References Cited

U.S. PATENT DOCUMENTS

| | | | | |
|---|---|---|---|---|
| 2012/0016440 | A1* | 1/2012 | Muccio | A61N 1/0452 607/48 |
| 2012/0265025 | A1* | 10/2012 | Hsiao | A61B 5/6801 600/300 |
| 2015/0148619 | A1* | 5/2015 | Berg | A61B 5/0024 600/301 |
| 2016/0228069 | A1 | 8/2016 | Derkx et al. | |
| 2017/0019988 | A1* | 1/2017 | McGrane | A61B 5/398 |
| 2017/0273590 | A1* | 9/2017 | Maesani | A61B 5/291 |
| 2017/0360329 | A1* | 12/2017 | Derkx | A61B 5/085 |
| 2018/0049678 | A1* | 2/2018 | Hoskuldsson | A61B 5/6823 |
| 2018/0307314 | A1* | 10/2018 | Connor | A61B 5/1123 |

FOREIGN PATENT DOCUMENTS

| | | | | |
|---|---|---|---|---|
| WO | WO-2015175904 | A1 * | 11/2015 | ........... A61B 5/0051 |
| WO | WO-2016120074 | A1 * | 8/2016 | ............. A61B 5/113 |

OTHER PUBLICATIONS

Sharina Helderop, "Draadloos Monitoren van Babys' Dankzij de Bambi-Belt," [Opgehaald op Mar. 9, 2017]; e52.nl/draadloos-monitoren-van-babys-met-de-bambi-belt/—Jul. 5, 2016 (5 pages).
Juliette V. Kraaijenga et al., "Diagnosis of Hemidiaphragmatic Paresis in a Preterm Infant with Transcutaneous Electromyography: A Case Report," Neonatology 2015; 108: pp. 38-41 (Published Online May 9, 2015).
Xiaoming Tao, "Handbook of Smart Textiles," Springer Reference, © Springer Singapore Heidelberg New York, Dordrecht London 2015 (9 pages).
Silbrecht Bouwstra, "Designing for the Parent-to-Infant Bonding Experience," Technische Universiteit, Eindhoven, Published Jan. 1, 2013 (70 pages).
Nederland Patent Office, Search Report in corresponding Netherlands Application No. 2017506, dated Mar. 13, 2017 (7 pages).
Duiverman et al., "Reproducibility and Responsiveness of a Non-invasive EMG Technique of the Respiratory Muscles in COPD Patients and in Healthy Subjects," Journal of Applied Physiology, American Physiological Society, US, vol. 96, No. 5, pp. 1723-1729, XP002390673 (May 1, 2004).
European Patent Office, International Search Report in corresponding International Application No. PCT/NL2017/050624, dated Jan. 17, 2018 (3 pages).
European Patent Office, Examination Report in corresponding European Application No. 17790860.5 dated Oct. 18, 2022 (8 pages).

* cited by examiner

WEARABLE DEVICE, METHOD AND SYSTEM FOR MONITORING ONE OR MORE VITAL SIGNS OF A HUMAN BODY

CROSS-REFERENCE TO RELATED APPLICATIONS

This patent application is a U.S. National Phase of PCT International Application No. PCT/NL2017/050624, filed Sep. 20, 2017, which claims priority to Netherlands Application No. 2017506, filed Sep. 21, 2016, which are both expressly incorporated by reference in their entireties, including any references contained therein.

FIELD OF THE INVENTION

The present invention is directed at a wearable device for monitoring one or more vital signs of a human body, the device comprising a carrier suitable for being worn around an abdominal part of the body, and an electrode arrangement comprising a plurality of conductive electrodes. The invention is further directed at a method for use with the wearable device, and at a system using the wearable device.

BACKGROUND

The present document is particularly concerned with medical aids for the nursing and caring of premature babies, i.e. babies having had a preterm birth. Preterm babies, i.e. babies that were born after a pregnancy of less than 37 weeks, are typically cared for by neonatal intensive care units (NICU) in hospitals, in isolation in an isolette (also referred to as 'incubator') while their vital signs are continuously monitored. Conventionally, such vital signs are monitored using conventional means for providing an electrocardiogram (ECG) and an electromyogram (EMG), such as to monitor their respiration and cardiac signal. Various alternatives are available for monitoring such signals.

An ECG is commonly provided using adhesive electrodes adhered to the babies body. Such electrodes are adhered to various parts of the body to detect different electrical physiological signals. For example, electrodes that may be adhered to the limbs and certain areas of the body are applied to form the Einthoven triangle, while electrodes in the thoracic area provide a main signal. Additional electrodes may be used to provide an EMG from which a respiratory signal may be obtained. Adhering of these electrodes is desired to ensure sufficient contact between the electrode and the skin, and to prevent accidental moving of the electrodes from their desired location on the body.

Although this method allows the baby's vital signs to be monitored in a reliable manner continuously, there are a number of disadvantages associated therewith. The main disadvantage is the adhering of electrodes to the skin of the premature baby. The skin of preterm babies is very sensible, and the use of adhesive electrodes is for that reason unpleasant and even harmful, and thus undesired. Removal of the electrodes hurts the baby, causing stress to both the baby and his or her parents. Such removal occasionally may even damage the skin, causing small wounds and increasing the risk of infection. Taking into account that typically the electrodes are to be replaced every few days (e.g. every five days), it may be understood that this disadvantage is not negligible—in particular for babies that are to be monitored over a period of multiple weeks.

Therefore, preferably the vital signs of premature babies are monitored in a different manner, which is more comfortable and less harmful to the skin. Alternative, non-contacting methods are either insufficiently reliable for medical purposes or are more invasive to the baby.

SUMMARY OF THE INVENTION

It is an object of the present invention to provide an alternative manner for monitoring vital signs of a baby, which alternative is easy to apply, more comfortable to the baby and less harmful to the skin, while enabling reliable detection of the baby's vital signs for medical purposes and continuous monitoring.

To this end, there is provided herewith a wearable device for monitoring one or more vital signs of a human body, the device comprising a carrier suitable for being worn around an abdominal part of the body, and an electrode arrangement comprising a plurality of conductive electrodes, wherein the electrodes are arranged on the carrier such as to be brought in contact with a skin of the body in use, and wherein the electrodes are arranged for receiving electric physiologic signals from the body for enabling monitoring of a membrane potential of one or more muscles in the body, wherein the electrodes comprise one or more first electrodes arranged on the carrier such as to be in contact with a side part of a torso of the body, such as to receive via said first electrodes a first electrical signal indicative of a membrane potential of a thoracic diaphragm of the body; wherein the carrier further comprises at least one second electrode in addition to the one or more first electrodes, the at least one second electrode being arranged on the carrier such as to be in contact with a mid front part of the abdominal part of the body, the at least one second electrode thereby being arranged for receiving a second electrical signal indicative of one or more further electric physiologic signals from the body, for enabling filtering of the first electrical signal using the second electrical signal for enabling electromyography of the thoracic diaphragm.

The wearable device of the present invention receives a first electrical signal which indicative of a membrane potential of a thoracic diaphragm, from one or more first electrodes located on a side part of the body (i.e. roughly an area below one or both of the arms) close to the location of the diaphragm muscle in the body. From this signal, in principle, an electromyogram can be made which allows the monitoring of a respiration signal indicative of the babies breathing pattern. However, typically the electric physiological signal from the thoracic diaphragm is very weak and distorted by many other signals from the body. For example, the cardiac signal is of much larger intensity and complicates the detection of a clear and reliable signal from the diaphragm movement. Also, many of the bodies physiologic processes (e.g. intestinal processes) and every movement made by the baby adds another source of distortion. Thus, in order to enable an EMG to be provided, the signal-to-noise ratio is to be improved such as to provide a reliable measurement.

In accordance with the present invention, a second signal is obtained from an area that is indicative of one or more further electric physiologic signals from the body. Preferably this second signal includes the physiological signals from as much sources of distortion as possible, or at least includes the main distortion signals, as this allows filtering of the first electrical signal using the second electrical signal to obtain the signal that reliably is indicative of the baby's vital signs. By such filtering the distortion signals can be effectively removed from the first electric signal. This can be done to such an extend that the diaphragm signal obtained is strong enough (having a sufficiently large signal-to-noise ratio) to allow the arrangement to be operable at higher contact impedances (between the electrode and the body) and bio-impedances (impedance of the skin itself). As a result, this obviates the need to adhere the electrodes directly to the skin to improve contact. All that is needed is continuous contact of the electrodes with the skin, which may be achieved in a different manner than by using adhesive electrodes.

In principle, the second signal may be obtained for example from an area on the body that is located remote from the thoracic diaphragm, where the diaphragm signal is weak. However, in the wearable device of the present invention, the second electrical signal is preferably obtained from a mid front part of the abdominal part of the body, to be aligned with the one or more first electrodes. This is based on the insight that in this area, a signal may be obtained wherein the distortion signals are strongly present whereas the signal from the diaphragm is weak (compared to the signal obtained from the side part of the body in the area under one or both arms). At the same time, due their aligned locations on the surface of the body, the one or more first electrodes and the at least one second electrode may optionally be attached to a same belt that is placed around the abdominal part of the body of the baby. This belt must in use be located at the level of where the diaphragm is located, to allow the first electrodes to pick up a strong enough signal indicative of the membrane potential of diaphragm. The use of a belt or similar carrier for the conductive electrodes (e.g. multiple interconnected belts, a harness, or even a vest) enables to put some pressure on the electrodes to ensure contact with the skin.

It is noted that the second electrical signal could, if desired, also be obtained at the same level on the back of the baby at the location of his/her spine. However, although this may provide a workable solution, additional effort would there be required due to the fact that the spine distorts all signals from the body and does also not provide a good contact area.

In addition to the detection of the EMG signal, the electrode likewise pick up the much stronger cardiac signal from which an ECG may be obtained. The signal may be filtered in a similar manner using the second electric signal to obtain a reliable ECG signal that can be used for medical purposes, such as for monitoring vital signs. Therefore, in accordance with an embodiment of the invention, at least one of the first electrodes, the at least one second electrode, or a further electrode of the conductive electrodes, is further arranged for receiving via said electric physiologic signals from the body, a further electrical signal indicative of a cardiac action potential for providing a heart rate signal. This enables to detect both the respiratory signal from the EMG as well as the cardiac signal from the ECG using the wearable device of the present invention.

In accordance with other embodiments, the carrier of the device comprises at least one of a belt, strap, harness or garment. This can be made in sizes to fit around the baby's body, or may also be made size adjustable or stretchable. However, in accordance with preferred embodiments, the carrier of the device is a single belt comprised by the device in absence of a further belt or carrier means, wherein all of the plurality of conductive electrodes is arranged on the single belt. In particular where the belt perfectly fits around the body of the baby, or can be made to fit perfectly e.g. by being size adjustable or stretchable, a single belt may be sufficient to fix the conductive electrodes to their desired locations by means of pressure from the perfect fitting belt. The wearable device is thereby easy to apply. To the baby, this is much more comfortable than the conventional manner of attaching adhesive electrodes. Moreover, due to the fact that the baby only needs to wear the belt with electrodes, the baby can be easily picked up by his or her parents, for example to be held for example by his or her mother. This is a very important aspect of bonding, making the baby feel safe and at ease, which is very difficult to arrange with the conventional manner of adhering electrodes (with wires to the analysis system) to multiple parts of the body. It is known that direct contact between mother and baby, is very important to the physical wellbeing of the baby, and has a positive effect on the baby's health. Moreover, as may be appreciated, the wearable device of the present invention (both the wired, but in particular the wireless variant) makes feeding in general, and breast feeding in particular, much easier and more comfortable for both the baby and the mother. This too is an important advantage of the present invention.

In some embodiments, one or more of the conductive electrodes are arranged on the carrier such as to protrude out of the carrier, for providing in use said contact between the skin and the electrode or electrodes. In these embodiments, due to the electrodes protruding from the carrier or belt, contact pressure will be slightly increased where the electrodes are located to thereby enable detection of a strong enough signal. For example, the electrodes may be embossed electrodes printed on the carrier or a layer thereof. For example, in accordance with some embodiments, the carrier comprises a stretchable material, and wherein one or more of the conductive electrodes comprise a layer of conductive material deposited on the stretchable material. Such deposition may be achieved using many kinds of known deposition methods, for example using printed electronics technology. In particular, in accordance with some embodiments, the one or more conductive electrodes are formed by one or more layers of silverchloride ($Ag_2Cl$), and wherein the stretchable material comprises a stretchable polyester, wherein the one or more layers of silverchloride are printed onto said stretchable polyester such as to protrude out of the carrier. Alternative stretchable materials may also be considered, for example a stretchable polyurethane (PU) or thermoplastic polyurethane (TPU) may be applied instead of or in addition to the stretchable polyester.

In accordance with some embodiments, the carrier comprises at least one sweat absorption layer, such as a layer comprising viscose fibers. This increases comfort for the baby wearing the device, and in addition can be made to protect the electrodes and electronic pathways from becoming moisty of sweat. As may be appreciated, sweat contains salts that cause it to be a reasonable well electric conductor. Therefore, the electronic pathways becoming moisty due to sweating may add to disturbance on the signal. Although this may be prevented by sealing the electronic pathways, the use of the sweat absorption layer to prevent sweat from reaching the electronics may provide a first line of protection while at the same time increasing comfort for the baby. For example, in accordance with some embodiments, the sweat absorption layer is arranged such as to cover a stretchable layer comprising the conductive electrodes and conductive paths for conveying electric signals from the electrodes, and wherein the sweat absorption layer comprises holes or cutout portions through which the conductive electrodes protrude for being in contact with the skin. The cut-out portions or holes allow the electrodes to be in contact with the skin.

In accordance with some embodiments, the carrier comprises an outer reinforcement layer, such as a polypropylene textile layer. This allows the carrier to fastened such as to provide sufficient pressure on the electrodes without breaking thereof. In use, around the abdominal part of the body of the baby, the exerted pressure on the electrodes must be limited to prevent discomfort to the baby. As will be understood, preterm babies are generally very fragile. Although some limited amount of pressure may be added to the electrodes via the belt or carrier, this should be just enough to receive a clear EMG and/or ECG signal. However, care must be taken not to cause discomfort, and certainly not to cause shortness of breath or even hurting the baby. Preferably, belts may for example be made available in different sizes, and may even additionally be size adjustable such as to be made to perfectly fit each baby.

In some embodiments, the carrier is a belt and one or more of it's layers, e.g. the reinforcement layer and a further layer, form an envelope for enclosing the flexible layer and the sweat absorption layer. This allows the internal functional layers of the belt, e.g. the sweat absorption layer and the flexible printed circuit board (PCB) including the electrodes, to be enclosed by the layers forming the envelope to keep them in place. Moreover, this also enables the belts to be fabricated easily, e.g. in large production. For example, the belts may be produced by aligning the various functional layers, inserting them in the envelope, and closing the envelope while fixing the layer and adding connection means.

In accordance with some further embodiments, the device further includes at least one of a group comprising: a signal connector element for enabling connection of conductive wires or plugs for conveying said electric physiologic signals; a wireless transmitter for enabling wireless communication of signals to a remote receiver; an amplifier for amplification of said electric physiologic signals; or one or more further sensors, such as further conductive sensors, a temperature sensor, an optical sensor, or an oxygen saturation (SpO2) sensor.

In particular the additional temperature sensor provides important additional information on the baby's health and physical wellbeing, by providing his or her skin temperature. Moreover, an amplifier enables pre-amplification of the received signals, e.g. to reduce the influence of noise sources during conveying of the signals to an analysis system. Moreover, an important advantage of the wireless transmitter is that it allows the wearable device to be made available in a wireless version. In that case, the baby only wears the carrier—e.g. the belt with electrodes—and is not attached to any wires. Although premature baby's do not move vigorously and are certainly not able to roll from their back to their belly to potentially become entangled in wires, providing a wireless version of the wearable device certainly improves the ease of use of the device and the level of comfort to both the baby and the parents.

In accordance with some embodiments, the carrier further comprises at least one element or a combination of elements of a group comprising: a size adjustable connecting part, such as a part comprising a fabric including a hooked surface arranged for adhering to a further fabric, for example Velcro; a size adjustable connector; a plurality of press studs; a plurality of buttons and one or more button holes; an elastic area. In particular where the carrier is a single belt, providing the carrier with a Velcro connecting part and an additional elastic area, provides an easy to apply wearable device. The amount of pressure exerted can be easily adjusted, while certifying good contact between the electrodes and the skin.

Preferably, the wearable device is provided in an application to monitor the physical state of babies, in particular preterm babies, as described so far. Therefore, in some embodiments, the carrier is a belt, and the belt has a length within a range of 100 to 600 millimeter, preferably within a range of 100 to 500 millimeter, more preferably within a range of 200 to 400 millimeter, such as to fit around an abdominal part of a body of a baby. As may be appreciated though, the manner of reliably measuring the ECG and EMG signals proposed in this document is not exclusively useable with babies, and may likewise be applied to monitor these signals in larger children or adults. With some anatomic adjustments, the method may even be applied to mammals other than humans.

In accordance with a further aspect, there is provided a method of monitoring one or more vital signs of a human body, the method comprising receiving, using a wearable device according to the first aspect described above, a plurality of electric physiologic signals detected using a plurality of conductive electrodes, wherein electric physiologic signals include at least a first signal and a second signal, the first signal being indicative of a membrane potential of a thoracic diaphragm of the body, the second electrical signal being indicative of one or more further electric physiologic signals from the body; and using an data processing algorithm for filtering of the first electrical signal using the second electrical signal for detecting the membrane potential of the thoracic diaphragm, for enabling electromyography thereof for providing a respiratory signal, and optionally for additionally detecting a cardiac action potential for providing a heart rate signal. In accordance with some embodiments thereof, this method may be encoded in instructions that may be made available through a telecommunications network, online storage, system on a chip or other computer readable medium, to cause a processor of an analysis system to perform the method of the invention while receiving the first and second signals from a wearable device as described above.

In accordance with a third aspect, there is provided a system for monitoring one or more vital signs of a human body, the system comprising a wearable device in accordance with the first aspect described above, further including a receiver for receiving electric physiologic signals detected using a plurality of conductive electrodes on the wearable device, wherein the system further comprises a processor, the processor being arranged for performing method in accordance with the second aspect. For example, the processor of the system may receive instructions as described above, that cause the processor to perform the method of the invention while receiving the first and second signals from the wearable device.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

DETAILED DESCRIPTION

The illustrations in the figures are provided for explanatory purposes only, such as to make clear the principles of the present invention and to support the detailed description below. The invention generally relates to a wearable device, in particular in it's preferred embodiment, a belt including electrodes arranged for cooperating with an analysis apparatus or system for detecting vital signs of a subject, e.g. a human or animal body, and in a particular embodiment a premature born baby. The invention also relates to a system and method for the acquisition and analysis of physiological data, such as for example but not limited to ECG, EMG, respiration and skin temperature using sensors integrated in a belt which is worn around the body of the baby. The invention further relates to a system with multiple sensors having an electrically conducting interface, an amplifier and a wireless transceiver. Moreover, the invention relates to a sensor array which may protrude out of the belt or may be integrated within: with each sensor having the capability to detect alone, the aforementioned physiological data, or in a network with other sensors on the belt. The invention also relates to a method of monitoring vital signs of a human body, to a computer program product available on a computer readable medium, and to an analysis system for monitoring vital signs of a human, in a particular embodiment a premature born baby.

The aim of the invention is twofold: (1) to provide a more comfortable solution for the baby because currently electrodes are attached with adhesives to the skin, which can damage the fragile skin of the baby, and (2) for the mother, because the belt improves the skin-to-skin contact between baby and mother, which results in better kangaroo-mother care.

Figure 1:
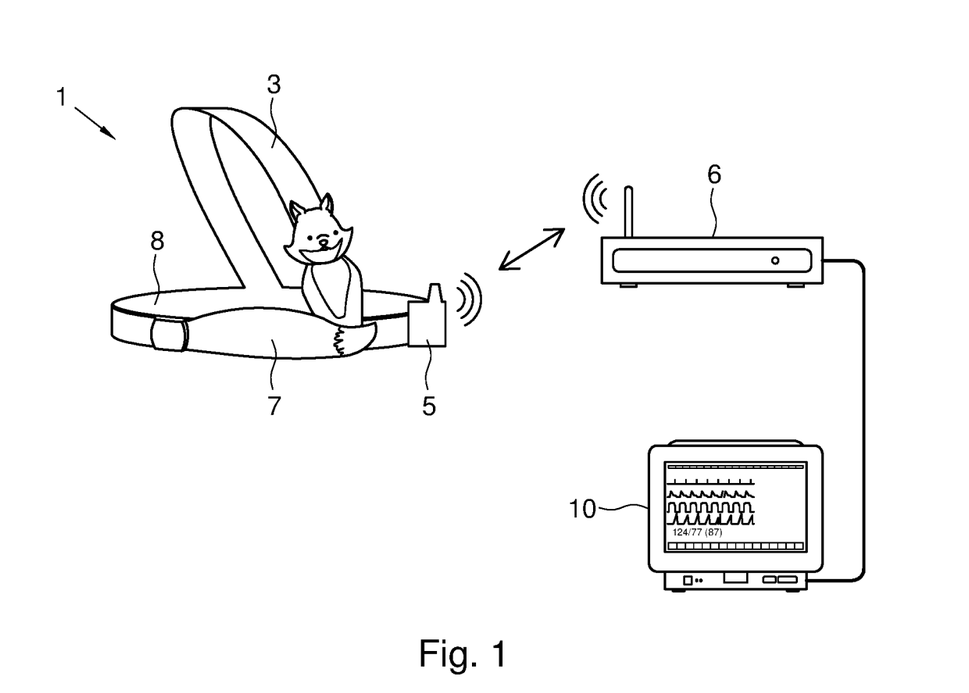
FIG. 1 schematically illustrates a system in accordance with the present invention, including a wearable device.

As illustrated in FIG. 1, a system 1 in accordance with an embodiment of the present invention, as a whole, consists of at least four parts. A wearable device 3 comprising a carrier 7, for example a belt 7, comprises a plurality of electrodes (not shown in FIG. 1) for sensing and receiving electric physiological signals from a body, e.g. a preterm baby. The conductive electrodes on the belt 7 for example provide integrated ECG, EMG and temperature sensors as will be explained further below. A transmitter 5 on the belt 7 captures and amplifies the signals from the conductive electrodes. These are transmitted by the transmitter 5 to a base station 6 which receives the signals. For example, the system may apply a standard IEEE 802.11 data transmission protocol (WIFI), or an alternative such as a standard IEEE 802.15.1 data transmission protocol (Bluetooth™). In particular, the system may apply a low power consumption data transmission protocol such as Bluetooth Low Energy (BLE or Bluetooth v4.0) or IEEE 802.15.4. The invention, however, is not limited to any specific data transmission protocol. The analysis system 1, e.g. a processor (not shown) in the receiving base station 6 or in another analyzer, processes the data into physiological signs. A patient monitor 10 displays and monitors the vital signs for the medical staff.

In FIG. 1, the carrier 3 is illustrated as a harness type garment, consisting of a belt 7 to go around an abdominal part of a baby's torso, and a strap that may go over the baby's shoulder. Alternatively, a full garment may be provided that covers a more substantial part of the baby's skin. However, preterm born baby's frequently are to be treated with phototherapy, requiring their skin to be exposed to light. For this reason, preferably the use of an as small as possible carrier that does not cover a large portion of the skin, is preferred. Therefore, the harness 3 of FIG. 1 is preferred over a full garment, whereas a single belt 7 without any further straps (unlike FIG. 1) is even more preferred. Such a belt 7 is for example illustrated in FIGS. 2b and 2c, 3, and 6a to 6d, to be described further below. Moreover, since preterm baby's (e.g. when phototherapy is desired) typically reside in an isolette or a room at increased ambient temperature, the risk of hypothermia of the body of the baby is diminished, and a full garment to prevent cooling thus is not needed.

Figure 2A:
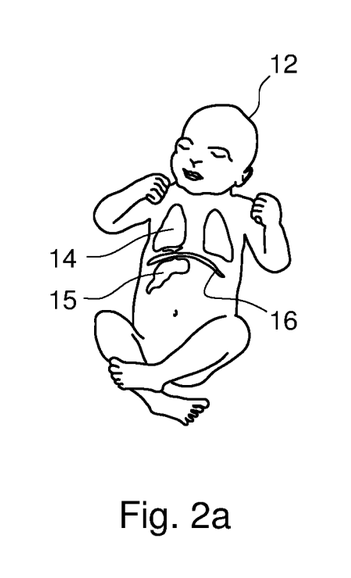
FIGS. 2a-2c schematically illustrate a wearable device in accordance with the invention and how it may be applied to a baby.
Figure 2B:
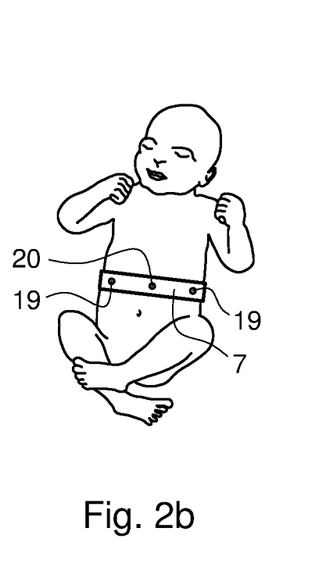
Figure 2C:
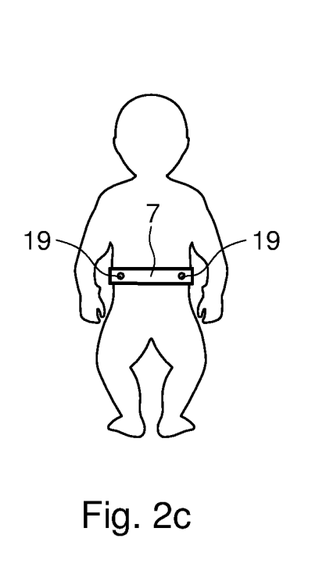

The function of the belt 7 is to provide a surface that enables the conductive electrodes 19 and 20 to be in direct contact with the body. Referring to FIG. 2, the belt 7 is placed on top of the lower part of the ribcage on the abdominal area of the baby 12, i.e. at the costal margin, at the border of chest and abdomen. This is important because the electrodes 19 need to be placed as close as possible to the diaphragm muscle 16 in order to measure the derived EMG breathing signal and ECG signal therefrom. FIG. 2a schematically shows the anatomy of the baby 12, including the relative locations of the lungs 14, liver 15 and thoracic diaphragm 16. The latter of these, the diaphragm 16 is slightly curved down (i.e. in the direction of the legs) towards the sides of the torso of the baby 12. The wearable device 3 in the embodiment of FIG. 2 consists only of a belt 7 serving as carrier for the conductive electrodes 19, 20 and other elements. The conductive electrodes include, in the present embodiment including a 4-channel ECG/EMG arrangement, four first electrodes 19 and a second electrode 20. Of the four first electrodes, two electrodes 19 are visible on the front side of the baby on the side (FIG. 2b). A further two electrodes 19 are visible on the back side of the baby (FIG. 2c). The number of each of the first or second electrodes may be different from what is described here (e.g. 8 first electrodes and 2 second electrodes; or one electrode of each type), but it is important that the wearable device of the present invention has at least one first electrode 19 and at least one second electrode 20. As may be understood, adding additional electrodes increases the yield of useable signals therefrom, however the belt 7 to be fitted around the body of a preterm baby does not provide to much room to add an unlimited amount of electrodes. It has been found that the embodiment shown, including four first electrodes 19 and a second electrode 20, provides a clear signal that can be filtered to yield a reliable EMG/ECG measurement to provide the vital signs.

In FIG. 2b, it can be seen that the first electrodes 19 are located to the sides of the torso, such as to be as close as possible to the location where the diaphragm 16 curves down. This location is suitable for receiving, by the electrodes 19, a signal including components that are indicative of a membrane potential of the thoracic diaphragm 16, from which an EMG may be created if the signal-to-noise ratio (SNR) is sufficiently large. Typically, however, many disturbance signals are present that prevent the SNR to be sufficient to provide an EMG. An ECG may be created though, because the cardiac signal has a larger intensity than the respiratory signal from the diaphragm 16. However, this is part of the problem, as it causes the respiratory signal from the diaphragm 16 to be almost invisible. This is resolved, in accordance with the present invention, by using the signal from a second electrode 20 to filter the signal from the first electrode 19. The second electrode 20 resides on the belt 7, such as to be in the mid part of the abdominal area of the body of the baby. This more or less coincides, as follows by comparing FIG. 2b with FIG. 2a, with the location of the apex of the thoracic diaphragm 16. Hence, the signal from the diaphragm 16 in this location is much weaker than in the area where first electrodes 19 are located on the belt 7. However, this is a very good location to obtain a second electric signal that is indicative of the most significant electric physiologic disturbance signals. Hence, the first electric signal from the first electrodes provide a much stronger diaphragm signal than the second electric signal from the second electrode. This allows filtering of the first signal by the second signal to yield—with sufficient SNR— the signal component that is indicative of a membrane potential of the thoracic diaphragm 16, from which the EMG may be created providing the respiratory signal.

Figure 3:
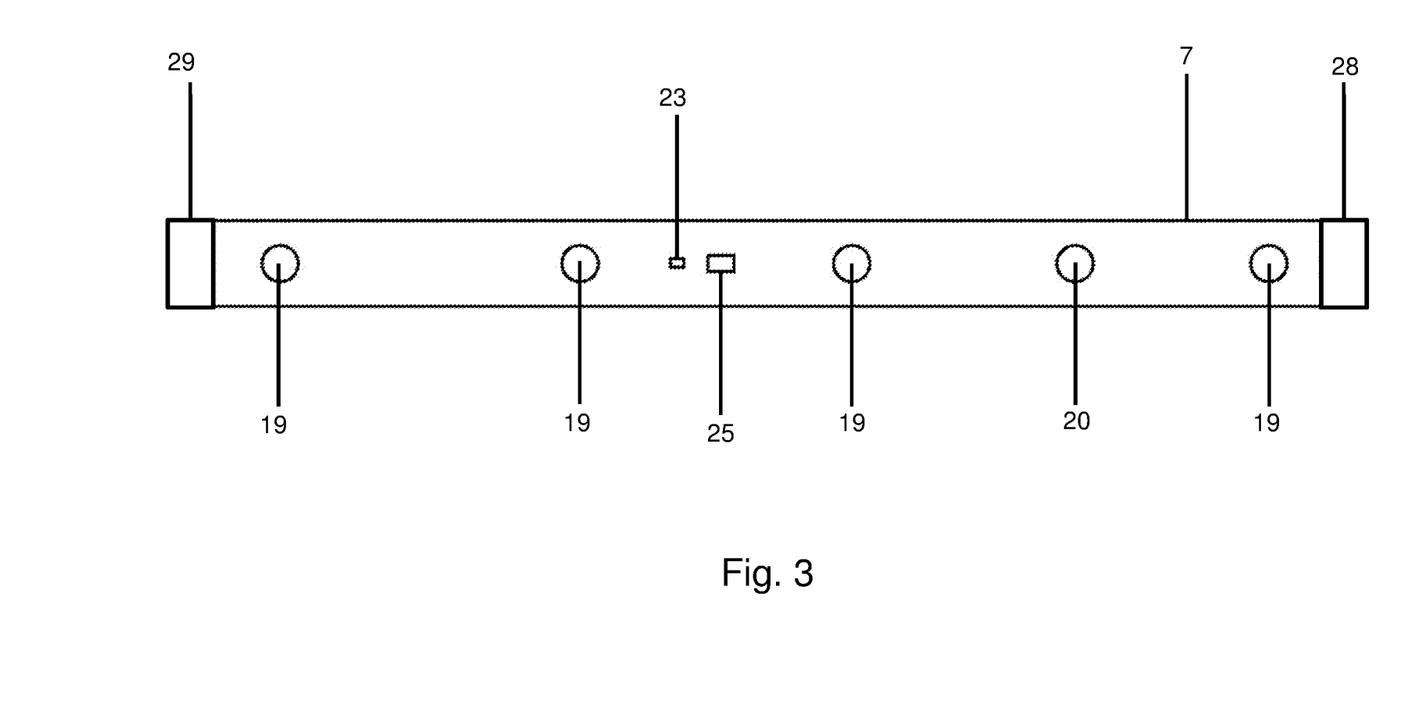
FIG. 3 schematically illustrates a wearable device in accordance with the present invention.

The wearable device 3 of the invention comprises, in accordance with the embodiment illustrated in FIG. 3, of four ECG/EMG electrodes 19 in a 4-channel configuration. From the electrodes 19, a respiratory signal is derived as described above. The device further comprises skin-based temperature sensor 23, providing a skin temperature measurement signal. FIG. 3 shows the configuration of the electrodes 19, 20 and sensors 23 on the belt 7. The area between the two electrodes 19 where the temperature sensor 23 is located, coincides with the right side of the baby's torso (as seen from the baby 12) and includes a connector 25. To the connector 25, plugs and wires may be connected to convey the electric signals from the electrodes 19 and 20 in a wireline configuration. In the preferred wireless configuration, the connection terminal 25 allows connection and fixing of the transmitter unit 5. As may be appreciated, the connection terminal 25 may be placed elsewhere on the belt 7, however in the location shown it is found to be least disturbing for the baby. On the left side area of the baby's body (the ultimate ends of the belt 7 in FIG. 3), mechanical connection areas, e.g. cooperating Velcro areas 28 and 29, allow closing of the belt 7 around the baby's body in an adjustable manner. As may be appreciated, other solutions are available that provide an adjustable connection area. Moreover, instead of or in addition to the size adjustable connector parts 28 and 29, elastic or stretchable areas may be applied to fit the belt 7 to a range of different sizes.

The electrodes 19, 20 used for ECG and derived EMG respiratory signal are printed with Ag2Cl ink on a stretchable substrate. Important factors that were considered are the following. The shape of the electrodes: based on recommendations by experts it was determined that circular electrodes 19, 20 are most fit for contact with the baby skin because there are no sharp corners. However, other this is not limiting on the invention, as other shapes of electrodes may likewise be applied. Regarding the size of the electrodes, it was found that the size of the electrodes is not important for the signal quality. The hardware (e.g. system 1 of FIG. 1) can work with high impedance (>100 kΩ), e.g. bio-impedance and contact impedance. However, it is important that the electrode touches the skin. An suitable size of the electrodes is between 5 mm and 10 mm (depending on the size of the belt, 5 mm for XS and S, 10 mm for M and L—see FIGS. 6a to 6d). Regarding the position of the electrodes, the determining factors for the electrode placement is that the sensors are located above the diaphragm muscles 16. This means that they are preferably located as far as possible on the side of the body, although electrodes placed in the area roughly underneath the arms may pick up a strong enough signal and thus may provide an workable system. Further, as explained, there is one common electrode positioned in the middle of the body that is used to filter noise. Regarding the height of the electrodes, the more contact the surface of the electrode has with the skin the better the signal reliability will be. An embossed electrode that has a higher position than the textile layer is preferred as it has more chance to be in contact with the skin.

The temperature measurement is used by the staff in the NICU to monitor the variations of the skin temperature of the baby 12. Therefore it is more important that the relative changes of the skin temperature are measured than the actual temperature, although of course both parameters will suffice. The belt 7 may contain a temperature sensor 23 provided using an NTC chip (negative temperature coefficient (NTC)) located above the liver 15 in the body of the baby 12. This chip may be placed on the back of the baby 12 next to the connector 25, assuming that there is not a lot of tissue between the back of the baby and the liver. As may be appreciated, the temperature or temperature change may be measured using a different type of sensor than an NTC chip, including analog, digital or printed sensors.

Important properties of a preferred embodiment of the belt 7 are: the use of skin friendly materials (biocompatible, following ISO 13485 standard), comfortable (soft), aesthetically pleasing & friendly design (colors, illustrations), minimal material use to allow for skin-contact between mother and baby, durable (used for a few days in incubator), and it should provide a stable carrier 3 for a printed electronics substrate used for carrying the electrodes 19, 20 and their pathways 30.

Figure 4:
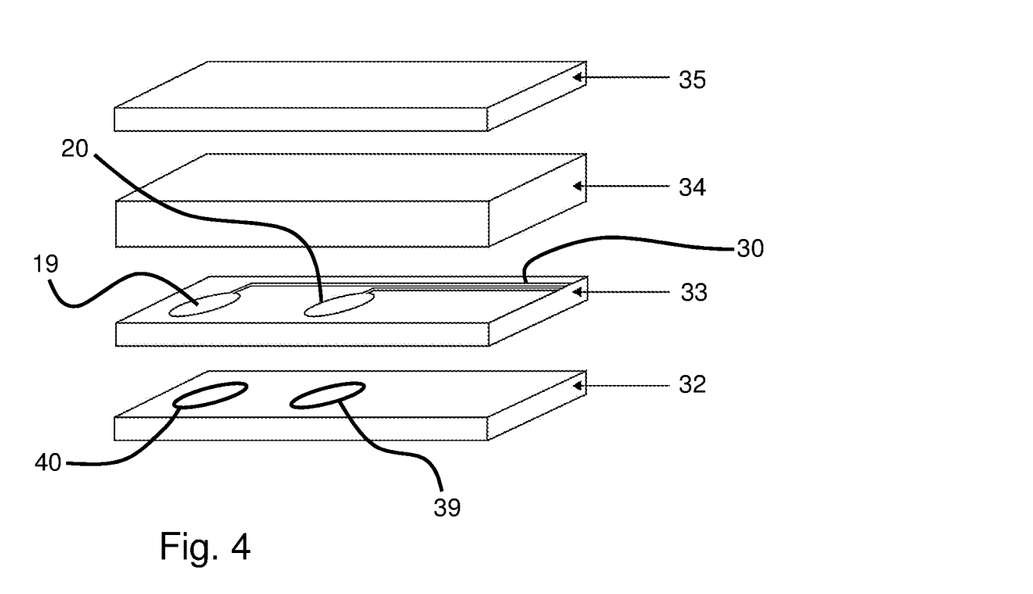
FIG. 4 schematically illustrates a layered internal structure of a wearable device in accordance with an embodiment.

FIG. 4 illustrates the structure of layers of the belt 7 of wearable device 3 in accordance with an embodiment. The belt 7 comprises layers 32, 33, 34 and 35 of synthetic non-woven textiles, that together provide the needed functionality. The outer layer 35 may be a polypropylene textile that gives strength to the belt 7, so that the other materials 32, 33 and 34 can be attached in the construction. The second layer 34, a thicker textile from Viscose fibres, is used to absorb sweat from the body and gives thickness and a soft feeling to the belt 7. The electrodes 19 and 20 and connections 30 are printed on a substrate 33 made from stretchable polyester which can be heat-bonded onto the Viscose layer 34. The electrodes 19, 20 are printed using silverchloride ($Ag_2Cl$) ink that can be layered to create a 3D embossed surface that presses against the skin. Finally, a thinner Viscose layer 32 covers the connections 30, but has openings 39, 40 to provide an opening for the electrodes 19, 20. In alternative embodiments, a stretchable polyurethane (PU) or thermoplastic polyurethane (TPU) may be applied instead of or in addition to the stretchable polyester, as the stretchable material on which the layer of conductive material is deposited for forming conductive electrodes.

Figure 5:
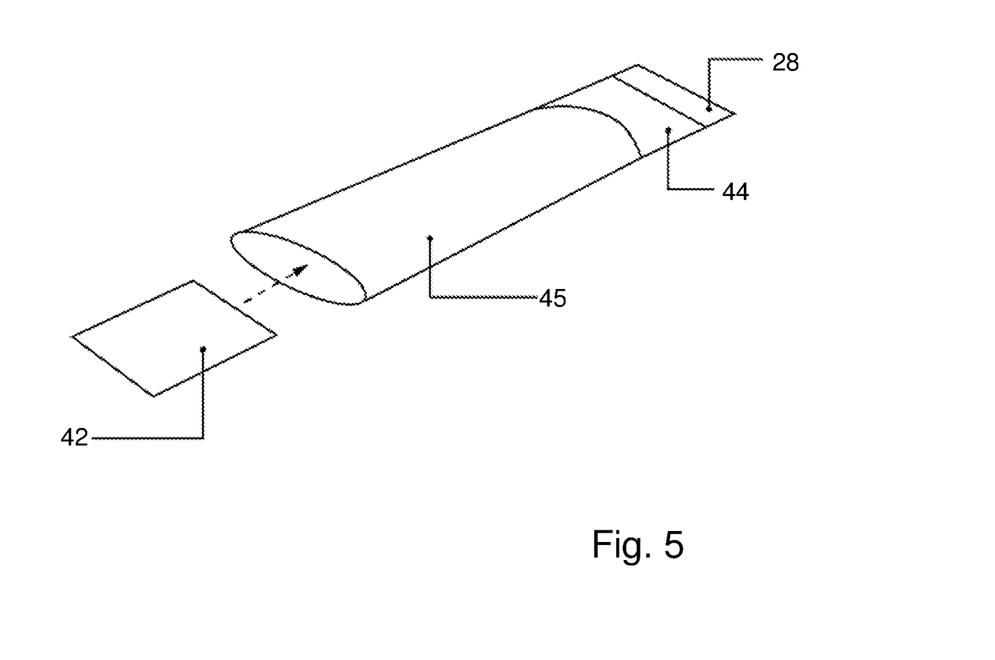
FIG. 5 schematically illustrates a wearable device in accordance with an embodiment, and how it may be constructed.
Figure 6A:
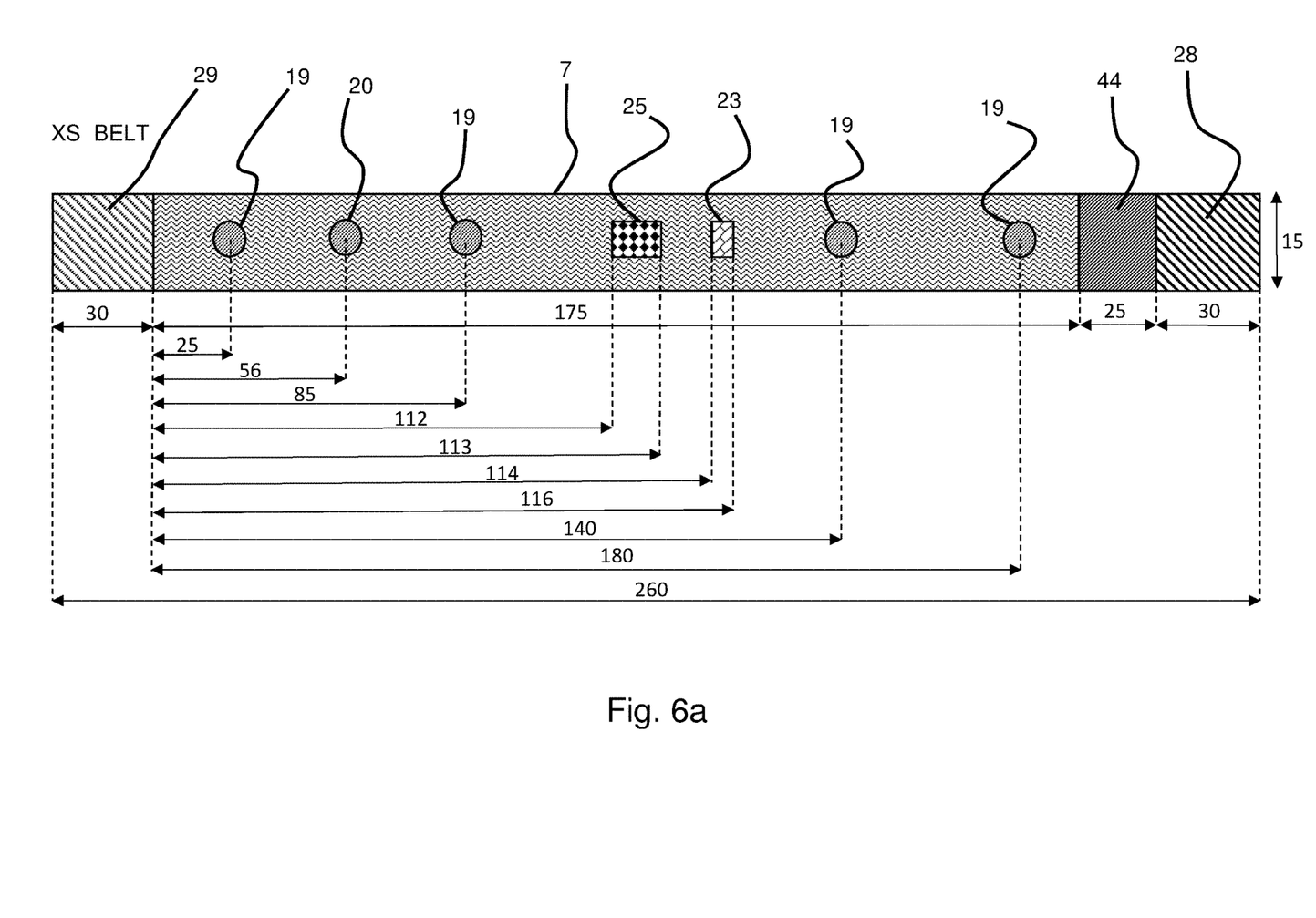
FIGS. 6a-6d schematically illustrate four different sized wearable devices in accordance with an embodiment.
Figure 6B:
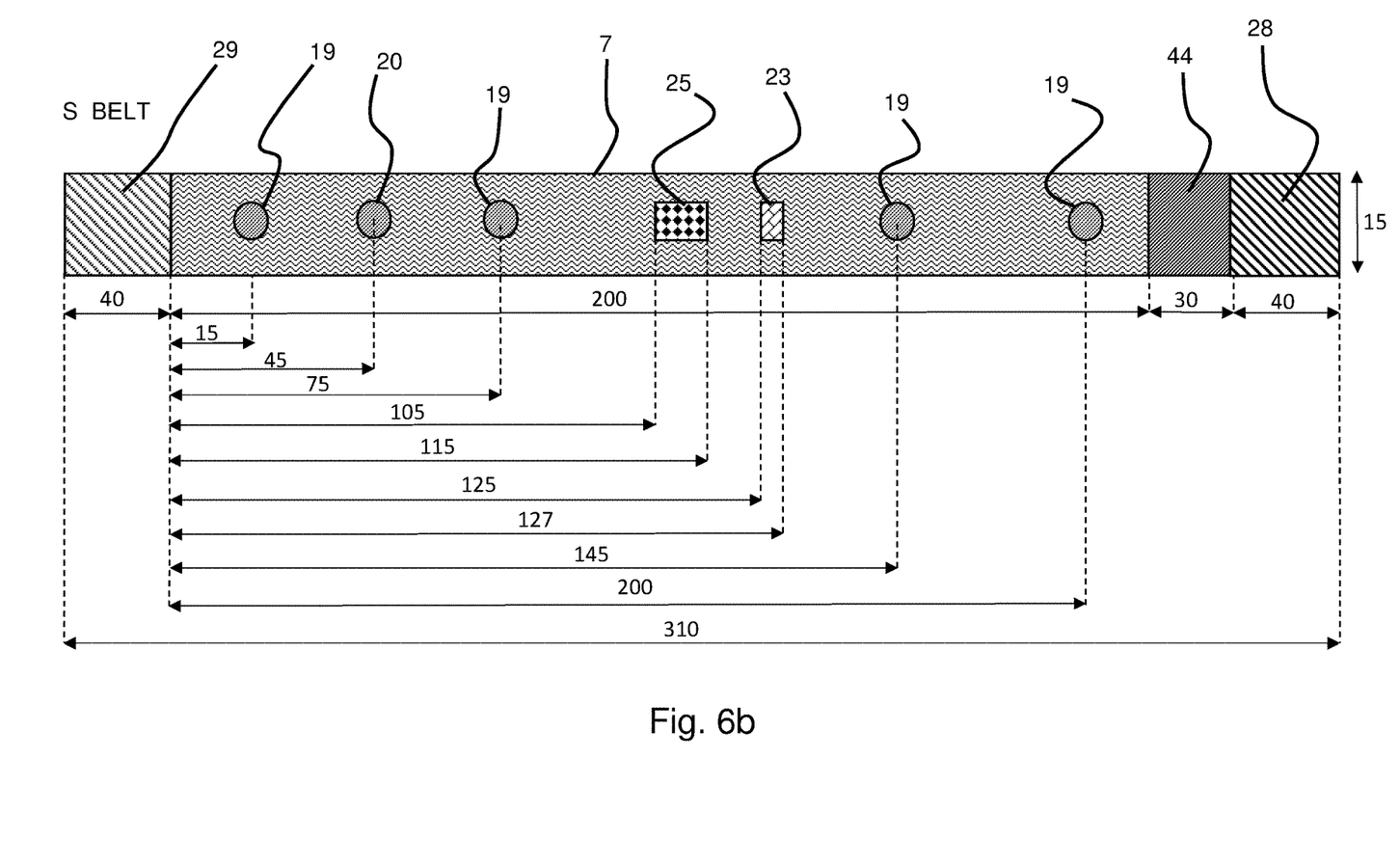
Figure 6C:
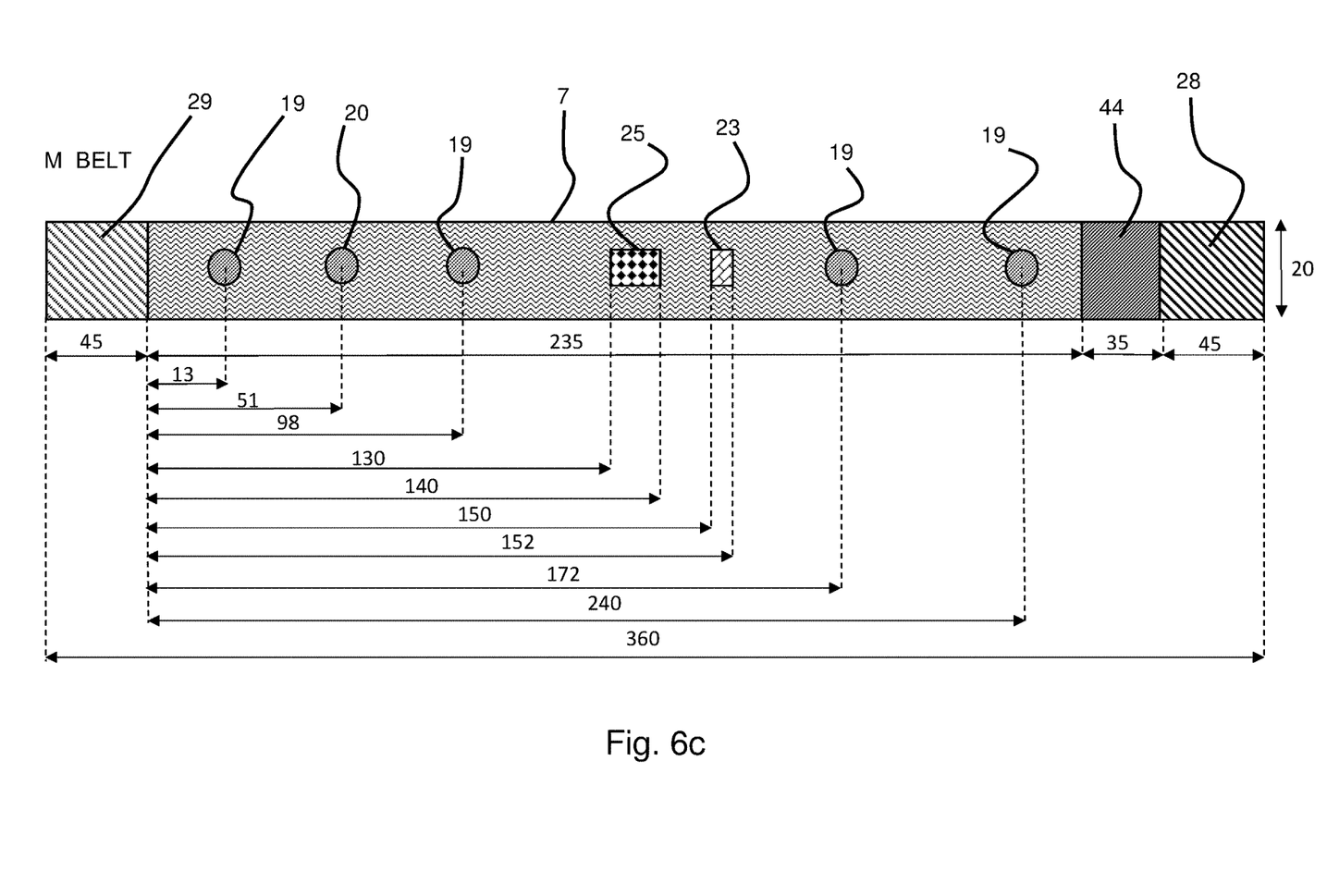
Figure 6D:
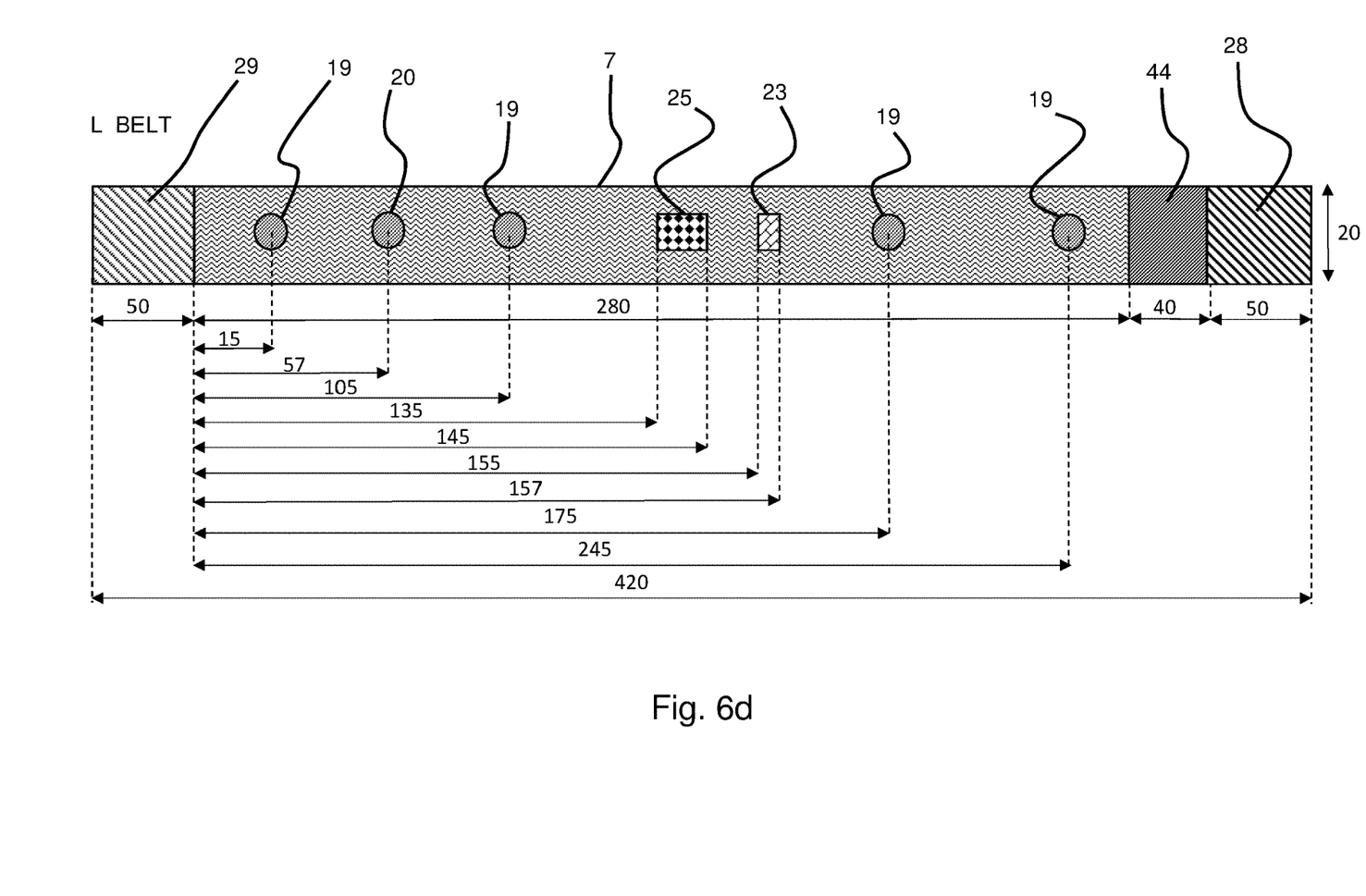

FIG. 5 schematically illustrates a construction of the belt 7. The two outer layers 35 and 32 of the belt are attached together through a heat bonding process (sealing or ultrasonic welding) to form an envelope 45 which can hold the thicker Viscose 34 and substrate 33 with printed electronics, shown as element 42. The belt 7 is attached around the body of the baby through a mechanical Velcro connection 28. An elastic area 44 is located between the Velcro connection 28 and the main part of belt 7 to provide extra elasticity and stretch.

The wearable device 3 of the present invention may be made available in various different sizes. For use around the body of a preterm baby, exemplary sizes are provided herewith; although it is to be noted that the invention is not limited to a specific size or certain dimensions. As stated above, the wearable device 3 may also be created to fit an adult, even though the present embodiments are directed at the preferred use with a preterm baby.

In the embodiments suitable for use with preterm babies, four ranges of belts 7 have been created. The size of the belt 7 depends on the size of the baby. There are some important parameters that were considered in the process (see Table 1), the baby chest circumference (based on measurements by nurses), the range to cover with the width of the belt (and thereby the elasticity which is necessary), the dimension of the diameter of the electrodes on the belt, the height of the belt, the length of the mechanical connection to close the belt.

TABLE 1

Overview of parameters used for various sizes of the wearable device (dimensions in millimeters).

| Size | Baby Chest Circumference | Belt should cover width Range | Electrode diameter | Belt Height | Connection Length (Velcro) |
|---|---|---|---|---|---|
| XS | 207 | 200-230 | 5 | 15 | 30 |
| S | 245 | 230-270 | 5 | 15 | 40 |
| M | 320 | 270-320 | 10 | 20 | 45 |
| L | 365 | 320-370 | 10 | 20 | 50 |

FIG. 6a to 6d show the dimensions used for different sized wearable devices 3 for use with preterm babies. The drawings are not in proportion with the actual dimensions, but the applied dimensions are indicated in the drawings in millimeters. These figures are for illustrative purposes only, and the invention is not limited to any specific size indicated. The reference numeral designate the elements described herein above.

The present invention has been described in terms of some specific embodiments thereof. It will be appreciated that the embodiments shown in the drawings and described herein are intended for illustrated purposes only and are not by any manner or means intended to be restrictive on the invention. It is believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention within its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the spirit and scope of the invention, as is determined by the claims. The invention may be practiced otherwise then as specifically described herein, and is only limited by the appended claims.

The invention claimed is:

1. A wearable device for monitoring one or more vital signs of a human body, wherein the human body is a baby, the wearable device comprising:

a carrier comprising a belt, wherein the belt has a length within a range of 100 to 600 millimeters to fit around an abdominal part of a body of the baby, and configured to be worn around the body while in use; and an electrode arrangement comprising a plurality of conductive electrodes including one or more first electrode and one or more second electrode, wherein the plurality of conductive electrodes are arranged on the carrier to be brought in contact with a skin of the body in use, and wherein the electrode arrangement is an electrocardiographic-electromyographic electrode arrangement wherein all electrodes of the plurality of conductive electrodes are configured for operating simultaneously to receive electric physiologic signals from the body for enabling monitoring of a membrane potential of one or more muscles in the body, wherein the wearable device is configured for performing electromyography of a thoracic diaphragm, wherein the one or more first electrode is arranged on the carrier to be in contact with a side part of a torso of the body near the thoracic diaphragm, the one or more first electrode being configured to cooperatively receive a first electrical signal indicative of the membrane potential of the thoracic diaphragm of the body and for providing the first electrical signal as a measurement signal;

wherein the one or more second electrode is arranged on the carrier to be in contact with a mid front part of the abdominal part of the body simultaneously with the first electrodes that receive the first electric signal indicative of said membrane potential of the thoracic diaphragm of the body, wherein each electrode of the one or more second electrode and the one or more first electrode is arranged aligned on the belt, such that the one or more second electrode is aligned with the one or more first electrode, the at least one second electrode thereby being arranged for receiving a second electrical signal indicative of one or more further electric physiologic signals from the body, wherein the second electrical signal in particular is indicative of a further membrane potential, and wherein the one or more second electrode is arranged for providing the second electrical signal separate from the first electrical signal, the second electrode thereby providing a filter signal, for enabling filtering of the first electrical signal using the second electrical signal for enabling electromyography of the thoracic diaphragm using only the first electric signal indicative of the membrane potential of the thoracic diaphragm and the second electric signal indicative of the further electric physiologic signals from the body.

2. The wearable device according to claim 1, wherein at least one of the first electrodes, the at least one second electrode, or a further electrode of the conductive electrodes, is further arranged for receiving via said electric physiologic signals from the body, a further electrical signal indicative of a cardiac action potential for providing a heart rate signal.

3. The wearable device according to claim 1, wherein the carrier of the wearable device comprises at least one of a belt, strap, harness or garment.

4. The wearable device according to claim 1, wherein one or more of the conductive electrodes are arranged on the carrier to protrude out of the carrier, for providing in use said contact between the skin and each of the conductive electrodes.

5. The wearable device according to claim 1, wherein the carrier comprises a stretchable material, and wherein one or more of the conductive electrodes comprise a layer of conductive material deposited on the stretchable material.

6. The wearable device according to claim 5, wherein the one or more conductive electrodes are formed by one or more layers of silverchloride ($Ag_2Cl$), and wherein the stretchable material comprises a stretchable polyester, wherein the one or more layers of silverchloride are printed onto said stretchable polyester to protrude out of the carrier.

7. The wearable device according to claim 1, wherein the carrier comprises at least one sweat absorption layer.

8. The wearable device according to claim 7, wherein the sweat absorption layer is arranged to cover a stretchable layer comprising the conductive electrodes and conductive paths for conveying electric signals from the conductive electrodes, and wherein the sweat absorption layer comprises holes or cutout portions through which the conductive electrodes protrude for being in contact with the skin.

9. The wearable device according to claim 8, wherein the carrier is a belt, and wherein one or more layers form an envelope for enclosing the flexible layer and the sweat absorption layer.

10. The wearable device according to claim 1, wherein the carrier comprises an outer reinforcement layer, a polypropylene textile layer.

11. The wearable device according to claim 1, wherein the wearable device further includes at least one further electronic component taken from the group consisting of:
- a signal connector element for enabling connection of conductive wires or plugs for conveying said electric physiologic signals;
- a wireless transmitter for enabling wireless communication of signals to a remote receiver;
- an amplifier for amplification of said electric physiologic signals; and
- one or more further sensors, further conductive sensors, a temperature sensor, an optical sensor, or an oxygen saturation (SpO2) sensor.

12. The wearable device according to claim 1, wherein the carrier further comprises at least one element or a combination of elements taken from the group consisting of:
- a size adjustable connecting part,
- a part comprising a fabric including a hooked surface arranged for adhering to a further fabric;
- a size adjustable connector;
- a plurality of press studs;
- a plurality of buttons and one or more button holes; and
- an elastic area.

* * * * *